United States Patent
Lehtomäki et al.

(10) Patent No.: US 8,742,095 B2
(45) Date of Patent: Jun. 3, 2014

(54) METHOD OF PRODUCING A BRAN PRODUCT

(75) Inventors: Ilkka Lehtomäki, Helsinki (FI); Olavi Myllymäki, Vtt (FI)

(73) Assignee: Valtion Teknillinen Tutkimuskeskus, Espoo (FI)

(*) Notice: Subject to any disclaimer, the term of this patent is extended or adjusted under 35 U.S.C. 154(b) by 515 days.

(21) Appl. No.: 12/919,974

(22) PCT Filed: Mar. 4, 2009

(86) PCT No.: PCT/FI2009/050177
§ 371 (c)(1),
(2), (4) Date: Nov. 24, 2010

(87) PCT Pub. No.: WO2009/109703
PCT Pub. Date: Sep. 11, 2009

(65) Prior Publication Data
US 2011/0065666 A1    Mar. 17, 2011

(30) Foreign Application Priority Data
Mar. 4, 2008   (FI) ................................ 20085205

(51) Int. Cl.
*C07H 1/06* (2006.01)
*C07H 1/08* (2006.01)

(52) U.S. Cl.
USPC ........................................................ 536/127

(58) Field of Classification Search
None
See application file for complete search history.

(56) References Cited

U.S. PATENT DOCUMENTS

| | | | |
|---|---|---|---|
| 5,063,078 A | 11/1991 | Foehse | |
| 5,082,673 A | 1/1992 | Inglett | |
| 6,020,016 A | 2/2000 | Castleberry | |
| 6,083,547 A * | 7/2000 | Katta et al. | 426/443 |
| 6,168,821 B1 | 1/2001 | Castleberry | |
| 2003/0147993 A1 | 8/2003 | Heddleson et al. | |
| 2004/0258829 A1 * | 12/2004 | Zheng et al. | 426/615 |
| 2006/0121131 A1 | 6/2006 | Redmond et al. | |

FOREIGN PATENT DOCUMENTS

| | | |
|---|---|---|
| EP | 0377530 B1 | 1/1995 |
| WO | WO 86/01080 A1 | 2/1986 |
| WO | WO 92/10106 A1 | 6/1992 |
| WO | WO 99/25198 A1 | 5/1999 |
| WO | WO 01/21012 A1 | 3/2001 |
| WO | WO 01/26479 A1 | 4/2001 |
| WO | WO 2004/099257 A1 | 11/2004 |
| WO | WO 2006/040395 A1 | 4/2006 |
| WO | WO 2008/006881 A1 | 1/2008 |

OTHER PUBLICATIONS

Barley Facts, Industry and product information, www.barleyfoods.org, downloaded from the internet May 22, 2013.*
International Search Report, PCT/FI2009/050177, mailed on Jun. 5, 2009.
Ralet et al., "Influence of Extrusion-cooking on the Physico-chemical Properties of Wheat Bran", Journal of Cereal Science, vol. 11, 1990, pp. 249-259.
Solihin et al., "Effects of Feed Moisture Content on Enzymatic Hydrolysis of Corn Starch in Twin-Screw Extruder and Saccharification of the Dried Extrudates", Food Sci. Biotechnol. vol. 16, No. 3, 2007, pp. 381-385.
Tapola et al., "Glycemic responses of oat bran products in type 2 diabetic patients", Nutrition, Metabolism & Cardiovascular Diseases (NMCD), vol. 15, Issue 4, Aug. 2005, 2 pages.
Tappy et al., "Effects of Breakfast cereals containing various amounts of beta-glucan fibers of plasma glucose and insulin responses in NIDDM subjects.", http://care.diabetesjournals.org/content/19/8/831.

* cited by examiner

*Primary Examiner* — Layla Bland
(74) *Attorney, Agent, or Firm* — Birch, Stewart, Kolasch & Birch, LLP (57) ABSTRACT

The present invention relates to a method of manufacturing a cereal bran product containing beta-glucan. According to the method, a plastic mass is formed from cereal bran by means of a thermo-mechanical treatment, and the mass is brought into contact with an enzyme that breaks up beta-glucan, with or without an enzyme that breaks up starch. After inactivating the enzyme, the bran is dried and, when so needed, ground. The cereal bran product manufactured according to the method has an essentially inextensible structure in a water environment. The product is suitable to be added to aqueous foodstuffs or to foodstuffs, the manufacture of which employs water.

16 Claims, 4 Drawing Sheets

Fig. 1

|  | Beta-glucan content in a drink, g per 100 g | Content of product fraction in a drink, g per 100 g | Content of beta-glucan in a wet product 1.) g per 100 g | Content of product fraction in a wet product, g per 100 g |
|---|---|---|---|---|
| FDA | 0.75 | NA | 0.75 | NA |
| According to the present invention | ≤2.0 | Extruded beta-glucan bran ≤12 | 4–10 | Extruded beta-glucan bran 20–50 |
| WO2006040395 (Laakso, Lehtinen) 2.) | ≤1.5 | Homogenized beta-glucan bran ≤8 | NA | NA |
| Keenan et al. (2007) (Barliv) | ≤1.0 | Beta-glucan extraction of barley ≤1.5 | NA | NA |
| US6020016 (Castleberry, Smucker) | ≤0.5 | NA | Only in the drink | Only in the drink |
| US6168821 (Castleberry) | ≤0.5 | NA | Only in the drink | Only in the drink |
| Oatly (commercial product) | 0.4 | Oatmeal 10 | NA | NA |
| Yosa (commercial product) | NA | NA | 0.5 | NA |
| Oatmeal porridge (100 g/0.5 l) | NA | NA | 0.9 | Oatmeal flakes 18 |

1.) The wet product comprises, for example, yoghurt, soup, porridge, pancake, filling, meat ball, pasta, etc.

2.) The homogenized product is often dried when used in dry products.

METHOD OF PRODUCING A BRAN PRODUCT

The present invention relates to a method according to the preamble of Claim 1 for manufacturing cereal bran that contains beta-glucan. The invention also relates to a product provided by the method and the use of the product.

Dietary fibre refers to carbohydrates that do not dissolve in the alimentary tract. They are also called non-starch polysaccharides or NSP compounds. The NSP compounds can be divided into water-soluble and insoluble fibres. An NSP compound especially important to health is the water-soluble beta-glucan, which is found in unprocessed cereals; oat, barley and rye, in particular. It has been proven that beta-glucan lowers the content of detrimental LDL cholesterol in blood serum, thus decreasing the risk of contracting cardiovascular diseases. Products containing beta-glucan can also decelerate the absorption of glucose into blood and, thus, keep the blood sugar constant for a long period of time. This, in turn, contributes to the feeling of fullness, thus helping in weight control.

As the health-promoting effects of the water-soluble NSP compounds have already been known for a long time, efforts have been made to develop products that contain these compounds. For example, the international patent application WO 2004/099257 of the same inventors describes a method, wherein the solubility of the NSP compounds is improved by crushing the cells that contain NSP compounds. The goal is to provide a cereal product that contains an increased amount of soluble NSP compounds. In later tests, it was observed that the cereal product obtained in this way decelerated the absorption of glucose into blood, also decelerating the increase in blood sugar caused by another carbohydrate that was consumed at the same time (Tapola et al. Glycemic responses of oat bran products in type 2 diabetic patients. Nutrition, Metabolism & Cardiovascular Diseases (2005) 15, 255-261.

A problem with adding soluble NSP compounds, such as beta-glucan, to foodstuffs is that, when adding beta-glucan in the form of, e.g., cereal bran, to foodstuffs containing plenty of water, the product becomes extensible and slimy. Naturally, such a structure is not desirable, e.g., in soups, yoghurts or drinks, which should be easy to spoon up or drink. Therefore, these products have mostly employed other dietary fibres, such as polyoligo saccharides and processed guar gum.

Efforts have been made to decrease the elasticity of the products containing beta-glucan by means of various methods. Naturally, the simplest method is to decrease the amount of the added beta-glucan, such as cereal bran containing beta-glucan. In that case, however, the desired health effects are not achieved.

The above-mentioned patent application WO 2004/099257 describes a method, wherein amylopectin starch was used to decelerate the dissolution of beta-glucan in a water environment. When the amount of starch rich in amylopectin in a product containing oat fibre was increased, the speed of dissolution of the finished product was considerably decelerated. When the portion of added starch was 25% of the amount of oat fibre, the viscosity of the product was low and the product maintained its particle-shaped structure in water for 60 minutes.

It is conceivable to reduce the elasticity by using structures, from which beta-glucan dissolves slowly. For example, dehusked grains can be used, which have high beta-glucan contents. The problem with the method is that it is difficult to control. Furthermore, the low dissolving speed or insolubility may cause the amount of dissolved beta-glucan to remain low.

It is also conceivable to reduce the elasticity by homogenization. This method requires a high water content. For example, in the patent application WO 2006/040395 A1, a suspension was provided by homogenization, wherein the content of dietary fibre was 2.1% by weight and the amount of beta-glucan 1.2% by weight (according to FDA, a content of 0.75 g/100 g has health effects). The viscosity of the suspension was 20-30% of the original viscosity that was achieved before the homogenization.

U.S. Pat. Nos. 6,020,016 and 6,168,821 suggest that the elasticity is reduced by adjusting the pH of the aqueous suspension. When using the methods according to these patents, the content of beta-glucan was 0.5 g/100 g of the liquid product at the most.

The published application WO92/10106 and the U.S. Pat. No. 5,082,673 describe a hydrolysis method for oatmeal and barley meal, wherein thermostable alpha-amylase was used to break up starch. The enzyme was inactivated after the treatment and the water-soluble fibre was separated from the water-insoluble fibre. However, breaking up the starch does not solve the problem with elasticity that is caused by the bran containing beta-glucan.

The published application US 2003/0147993 uses a 1→4 beta-glucanase enzyme, such as the Laminex BG and Multifect B enzymes, to break up the beta-glucan. The publication states that bile acids were bound to the beta-glucan molecules, which in an enzymatic process were broken up to a size category of below 50 000 daltons, more preferably 500-2500 daltons. The application states that this is preferable for the cholesterol metabolism.

The published application WO 99/25198 describes foodstuffs and drink mixtures that contain intermediate products, which contain extruded fibre. The products contain a source of soluble and insoluble fibre. The soluble fibre preferably originates from psyllium and the insoluble fibre from a starch-bearing cereal, such as oat bran, for example.

One problem with the solutions according to the known technology is that the content of beta-glucan remains so low that the desired health effects are no longer achieved or that large amounts of water must be used in the methods. Water removal is difficult and incurs costs. Many methods according to the known technology are also difficult to control.

The present invention endeavours to solve at least some of the problems according to the known technology.

It is an object of the present invention to provide a method, wherein the behaviour of the beta-glucan-bearing cereal bran is changed so that a structure is preferably provided that is inelastic in a liquid environment, particularly in a water environment, in an economic way. Another object of the present invention is to provide a cereal bran product that has an essentially inelastic structure in the water environment.

The present invention is based on the fact that the cereal bran is treated by various treatments, so that the structure of the bran takes a form, wherein the enzymes are allowed to act on it; however, so that the water content of the cereal bran remains low. By means of the various treatments, a mass can be formed from the cereal bran, wherein the molecular weight of the beta-glucan is decreased by breaking it up by means of enzymes in a controlled manner. Using the mass produced by the method according to the invention, a dry beta-glucan-bearing cereal bran product can be provided in a controlled and profitable manner, the product providing an inelastic structure in the liquid environment. Although the water content of the mass is low, the enzymes are capable of acting on the beta-glucan when the enzyme-containing water is evenly distributed in the thick mass. The water content of such a thick mass is so low that water cannot be separated mechanically from the same. The effect of the enzymes that break up the beta-glucan is considerably enhanced and accelerated by means of the enzymes that break up the starch.

More specifically, the method according to the invention is mainly characterized in that which is presented in the characterizing part of Claim 1.

The method according to the present invention can be used to provide a dry beta-glucan-bearing cereal bran product, which produces an inelastic structure in a liquid environment. The product is suitable to be used in fresh products of the food industry, such as drinks, yoghurts, fools, soups and similar aqueous products, and cosmetics. The product manufactured according to the invention has several health effects, such as a capability to decelerate the absorption of glucose into the blood.

The product can also be used in pharmaceutical preparations.

In the following, the invention is described in detail by means of the appended, detailed description and examples.

The present invention relates to a method of manufacturing a cereal bran product containing beta-glucan, preferably comprising the following stages:
1. The cereal bran is pre-treated, whereby the beta-glucan is brought out of the cereal bran;
2. the cereal bran is thermo-mechanically treated and brought into contact with the enzyme that breaks up the beta-glucan, with or without the enzyme that breaks up starch;
3. the enzyme(s) is (are) inactivated; and
4. the product is dried and, optionally, ground.

After the treatments, the cereal bran product is recovered.

At the first stage of the method, the cereal bran is pre-treated, whereby the beta-glucan contained in the cereal bran is brought out. The pre-treatment stage is important, because if the beta-glucan cannot be influenced by the enzyme or it is insensitive to the forces of the thermo-mechanical stage, the beta-glucan that is under the shelter of the structures remains untreated, and the desired change is not controlled. The beta-glucan can be brought out, e.g., by crushing the cereal bran by means of mechanical energy into particles, so that in connection with the crushing, at least the majority of the cells of the material that contain beta-glucan are damaged.

A method of bringing beta-glucan out is described, e.g., in the international published patent application WO 2004/099257. In the method described in the WO publication 2004/099257, over 50%, preferably over 90% of the cells of the material that contain beta-glucan are fractured, split or broken, so that the non-starch polysaccharides contained in them, including beta-glucan, are released into contact with the medium that dissolves the same. The cereal bran is preferably crushed into a particle size of below 100 μm, more preferably below 50 μm and most preferably below 20 μm. A corresponding method is also described in U.S. Pat. No. 5,063,078. A preferable particle size is smaller than the size of the cells of the material to be crushed, whereby even the smallest cell structures break and the effective content of the intracellular components, which are to be dissolved, increases in relation to the dissolving medium and the solubility is enhanced. The pre-treatment can be carried out by the combined effect of heat, pressure and shearing forces by, for example, extruding or expanding at a low moisture content or by homogenizing the material in the presence of extra water by repeating the pressure adjustments and/or times of homogenization, until the total energy amount required is applied to the material. An advisable use of energy in the extrusion is 0.15-0.39 kWh/kg of material.

The mass that is generated in the extrusion, wherein the original material is crushed, can be formulated into the desired grain size and shape after drying. A preferable intermediate product is obtained, when the moisture of the pre-treated material is first adjusted to a value of 6% by weight or 13% by weight, at the most. Suitable treating conditions are presented in the above-mentioned published application WO 2004/099257.

According to another embodiment, the beta-glucan of the bran can be brought out by grinding it when dry, so that at least 95% of the material is smaller than 200 μm and over 50% is smaller than 50 μm. Such a product is, for example, the barley bran that is mentioned in U.S. Pat. No. 5,063,078 or oat bran that is ground into a fine form in a similar manner.

The term "extrusion" refers to heating an oat product in a tube that is heated, inside of which there is a rotating screw for moving the product through the tube. At the tail end of the tube, there is a nozzle, through which the screw pushes the product. The structure of the screw can be different, so that there is a blocking screw at the tail end, for example. The properties of the product, the nozzle and the screw structure influence the pressure in the tube. While heated on the outside, water is added to the product inside the tube. Heating and the amount of water also influence the pressure.

An expander has a similar structure as an extruder, but the counter pressure at the tail end is provided, for example, by a hydraulic valve.

According to a preferred embodiment of the invention, a plastic mass is formed from the cereal bran by means of thermo-mechanical treatment after the pre-treatments. This can be influenced at the thermo-mechanical treating stage by the forces of the extrusion or the expander and by the substances added, such as enzymes or materials containing them, such as malt.

In the extrusion and the expander, the thickness of the mixture increases, the porous part decreases and almost disappears, and the reaction surface that is exposed to enzymatic effects grows. During the thermo-mechanical processing, the enzyme hydrolysis can be controlled and it is repeatable, whereby a controlled change in viscosity can be achieved in the end product.

When so desired, a trainer, where the bran is moistened and heated, can be used before the thermo-mechanical treatment.

At its simplest, the "trainer" is a screw conveyor, which can be heated and to which water or steam is added. The trainer may also consist of, e.g., two parallel or successive screws for providing the desired conditions. Such conditions can comprise, for example, sufficient mixing and a steady provision of heat and moisture.

At the thermo-mechanical processing stage, the enzyme that breaks up beta-glucan and the beta-glucan are brought into contact with each other. Furthermore, it is preferable to use an enzyme that breaks up starch, such as alpha-amylase. The conditions should be such that the enzymes are capable of functioning. The enzymes used preferably comprise enzymes that contain beta-glucanase (e.g., cellulase, hemicellulase, xylanase) or a material containing the same, such as malt. In addition, it is preferable to use alpha-amylases, particularly those that function under the same conditions as the beta-glucanase used. The thermo-mechanical treatment can be carried out, for example, by the extruder or the expander. The extruder is preferably used with or without the trainer.

According to a preferred embodiment of the invention, the thermo-mechanical treatment is carried out by means of double extrusion. In that case, the extrusion is preferably carried out in at least two stages, between which there is a delay. At the first extrusion stage, the cereal bran is brought into contact with the enzyme that breaks up beta-glucan. At the delay stage, the enzyme that breaks up beta-glucan is allowed to hydrolyze the beta-glucan in the bran. At the second extrusion stage, the enzyme is inactivated.

According to a second preferred embodiment of the invention, the thermo-mechanical treatment is carried out by single extrusion. In that case, it is preferable to use amylase in addition to the enzyme that breaks up beta-glucan. The hydrolysis by enzymes is preferably carried out at the initial and the middle stages of the extruder tube. The enzymes are preferably inactivated at the end of the extruder tube.

Figure 1:
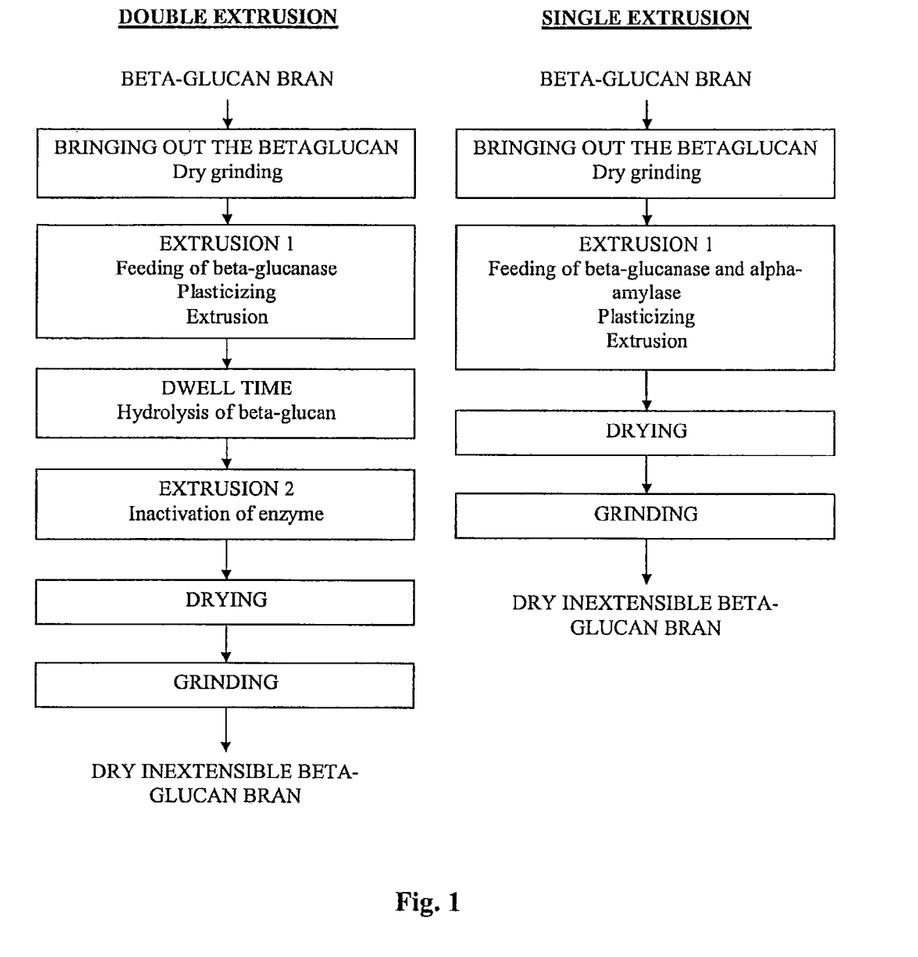
FIG. 1 shows the processing stages of bran in double extrusion and single extrusion.
Figure 2:
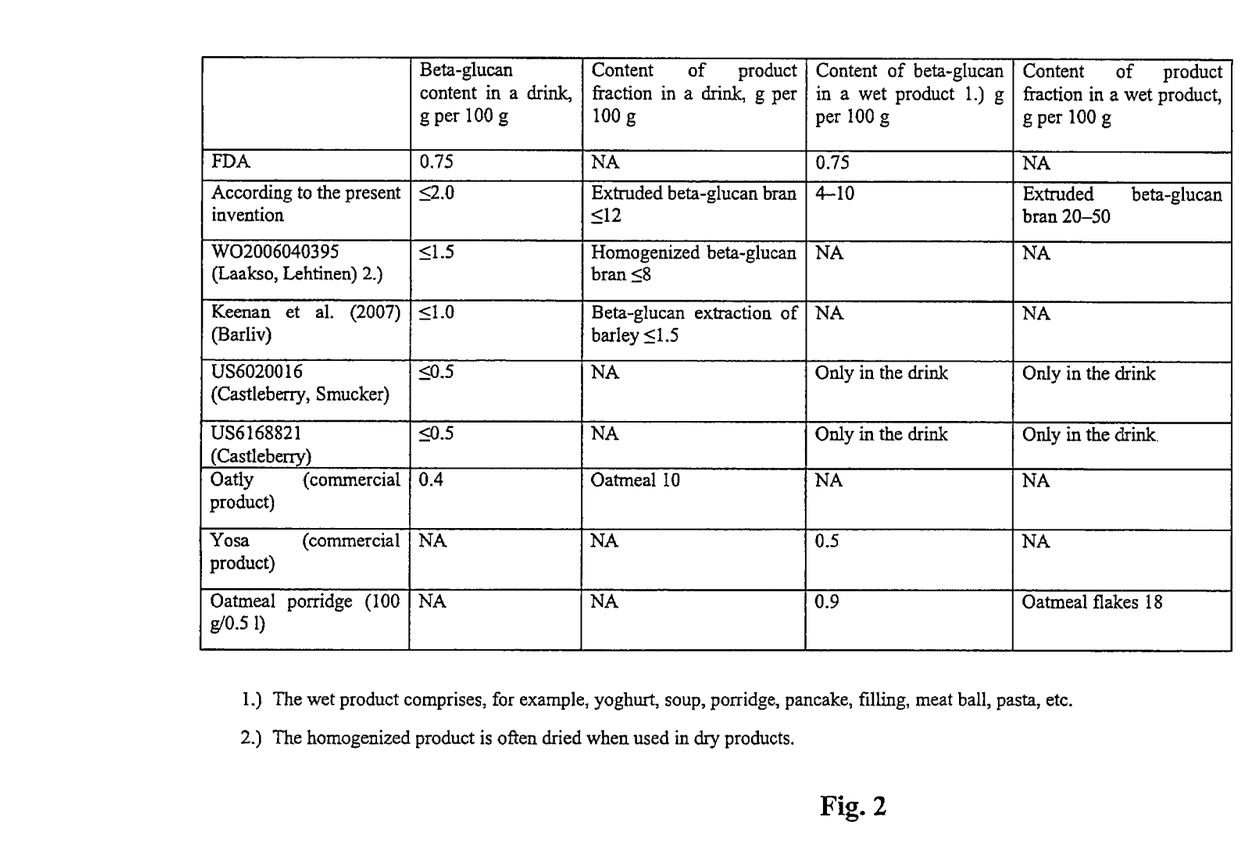
FIG. 2 compares the beta-glucan contents of brans, which are treated in different manners, in products containing water.

The main stages of the preferred embodiments of the invention are shown in FIG. 1. When the thermo-mechanical treatment is carried out by double extrusion, the moisture is preferably kept within 20-65% by weight, typically 20-60% by weight during the thermo-mechanical treatment. The temperature is preferably kept within 40-65° C., typically 50-65° C., most preferably at about 65° C. The treatments are carried out at the pH of the bran, which is about 6; therefore, the pH does not need to be adjusted. The portion of plastic mass from the volume of the extruder should be as large as possible. The velocity of the screw of the extruder or expander is not particularly significant, as it is not easy to transfer energy to the plastic mass. A low velocity of the screw ensures the longest possible time of effect for the enzyme.

The enzyme is dosed, for example, along with the added water to the front end of the extruder or the expander. The dose of the enzyme comprises about $1 \times 10^6$-$1000 \times 10^6$, preferably $10 \times 10^6$-$500 \times 10^6$ units of beta-glucanase, typically $50 \times 10^6$-$200 \times 10^6$ units of beta-glucanase an hour per tonne of bran that is treated. The beta-glucanase unit (BU) is the amount of enzyme, which under standard conditions (pH 4.8; 50° C.) produces one nmol of reducing sugars from the beta-glucan of barley, as glucose, in one second. In international units, BU corresponds to the amount of enzymes that produces 0.06 μmol of reducing sugars a minute.

The dwell time, whereby the enzymes hydrolyze beta-glucan is preferably 10 min-2 hours, typically 10-90 minutes.

For example, Econase® CE (AB Enzymes GmbH) can be used in an amount of about 0.1-3 litres, more preferably about 0.5-2.5 litres, typically about 1-2 litres an hour per tonne of bran. Other enzyme preparations containing beta-glucanase can be used in amounts that provide the corresponding beta-glucanase activity.

For the treatment, enzymes can be used, which are prepared by means of natural or genetically modified microbe strains. The enzymes can be produced by means of moulds or bacteria.

The enzyme activities are destroyed at the end of the thermo-mechanical processing stage by a suitable inactivation method of enzymes, e.g., by means of temperature. It is preferable to increase the temperature to 90-130° C., e.g., to about 95° C. The moisture is preferably within 20-65% by weight. The enzymes can be inactivated, for example, at the end of the extrusion or expander by raising the temperature of the plastic mass so high that the enzyme activity is destroyed.

After destroying the enzyme activity, the product is dried. The thermo-mechanically treated mass, which has no enzyme activity, is preferably dried at about 90-130° C. Drying is preferably carried out to a moisture content of within 5-14% by weight, more preferably about 12% by weight or less (the activity of water is below 0.6), most preferably 8% by weight or less.

Thereafter, according to the respective end use of the product, the product can be ground into the required particle size.

When the thermo-mechanical treatment is carried out by single extrusion, the moisture is preferably kept within 40-65% by weight, typically 45-55% by weight during the thermo-mechanical treatment. The temperature is preferably kept within 50-70° C., typically 60-68° C., most preferably at about 65° C. The dwell time, when the enzymes hydrolyze the beta-glucan and starch, is preferably 30 sec.-2 min, typically 50-80 sec. The treatments are carried out at the pH of the bran, which is about 6; therefore, the pH does not need to be adjusted.

The enzymes are dosed in a manner similar to that described above, e.g., along with the added water to the front end of the extruder or expander. The enzyme is dosed in an amount of $1 \times 10^6$-$1000 \times 10^6$, preferably $10 \times 10^6$-$500 \times 10^6$ units of beta-glucanase, typically $50 \times 10^6$-$200 \times 10^6$ units of beta-glucanase an hour per tonne of bran that is treated. The beta-glucanase unit (BU) is defined as described above in connection with the double extrusion.

Alpha-amylase, preferably thermophilic alpha-amylase, is used in an amount of about $10 \times 10^3$-$1000 \times 10^3$ KNU-T, preferably $50 \times 10^3$-$700 \times 10^3$ KNU-T units, typically 100-500 KNU-T (or KNU(S)) an hour per tonne of bran that is treated. One KNU-T is the amount of alpha-amylase, which under standard conditions (pH 7.1; 37° C.) turns 5.26 g of starch (k-a) (Merck Amylum soluble No. 9947275 or an equivalent thereof) into dextrin in an hour.

One KNU-T corresponds to an amount of alpha-amylase, which hydrolyzes 672 micromoles or ethylidene-$G_7$PNP in a minute under standard conditions (pH 7.1; 37° C.). The alpha-amylase hydrolyzes ethylidene-$G_7$PNP into G2PNP and G3PNP (G stands for glucose and PNO for p-nitrophenol). G2PNP and G3PNP are hydrolyzed by means of the alpha-glucosidase, which is added to the reaction mixture, into glucose and p-nitrophenol. Para-nitrophenol is measured by spectrophotometry at 405 nm. The definition of the alpha-amylase activity and that of the KNU(S) units are also described in the patent application WO2008/006881.

Typically, the beta-glucanase enzyme is obtained, for example, from the Econase CE product of AB Enzymes GmgH, and the alpha-amylase can be, for example, Termamyl® SC, from the Novozymes A/S product. Each enzyme is preferably used in an amount of about 0.1-3 litres, more preferably about 0.5-2.5 litres, and typically about 1-2 litres an hour per tonne of bran to be treated. Other enzyme preparations containing beta-glucanase of alpha-amylase can be used in amounts that provide the corresponding enzyme activities. Other suitable alpha-amylase products include Amylex or the alpha-amylases produced by the *Bacillus licheniformis, B. amyloliquefaciens*, or *B. stearothermophilus* species, particularly thermophilic amylases. Suitable beta-glucanase enzymes are typically produced by various species of the *Trichoderma* genus, particularly *T. reesei*. The enzymes are used in the required amounts under conditions that are optimal for the enzymatic action.

The enzymes are inactivated at the end of the extrusion tube by keeping the temperature at 90-130° C., preferably at about 95° C. The moisture is preferably within 20-65% by weight.

The thermo-mechanically treated mass, which has no enzyme activity, is dried as described previously in connection with the description of double extrusion.

The present invention can employ the above-described or other enzyme preparations that break up beta-glucan and starch, in necessary amounts and under conditions optimal for the enzyme activity. For the enzyme treatments according to the invention, enzymes can be used, which are prepared by means of natural or genetically modified strains. The enzymes can be produced by moulds or bacteria.

The raw material of the method according to the invention can be any cereal fraction containing beta-glucan, such as the grains of oat, rye or barley or their fractions; however, particularly barley or oat bran. In particular, the invention enables the use of bran, the beta-glucan content of which is high, over 15% by weight of the dry matter. Such cereal bran contains 15-40% by weight of β-glucan and 5-35% by weight of starch. Such a material is described, for example, in the patent specifications WO 0126479 and EP 0 377 530. The high beta-glucan content enables the use of minor amounts of bran to achieve physiologically significant amounts of beta-glucan. Furthermore, it is easy to use the bran in the manufacture of, for example, drinks, yoghurts, fools and perishable goods without impairing their structure.

The viscosity of the end product can be influenced in a controlled manner by adjusting the moisture, temperature and dwell time of the process. The product was assessed for the development of its viscosity as a function of time and shear rate.

The extensibility properties of the product can be assessed, for example, by a test, wherein the suspension of 7% by weight of the end product (about 1 g of beta-glucan per 100 g of suspension) was boiled and cooled and the extensibility was estimated visually. An excess of amylase was added to the extensibility test, not containing beta-glucanase. Consequently, the extensibility is developed by the beta-glucan only.

The dry bran product containing beta-glucan, obtained by the method according to the present invention, can be added to foodstuffs containing water, so that the amount of beta-glucan is preferably 4-10 g/100 g, typically 2-5 g/100 g, whereby the obtained product has an essentially inextensible structure.

When comparing the beta-glucan contents, which are obtained in the products by the method of the present invention, with the contents that are provided in the products by the methods of the known technology, and with those in commercial products, it can be observed that the highest beta-glucan content is obtained in the products by the method of the present invention without impeding the structure of the foodstuff, in which the product is used. The beta-glucan contents of the products for oat and barley bran manufactured in different ways are shown in Table 2.

Figure 5:
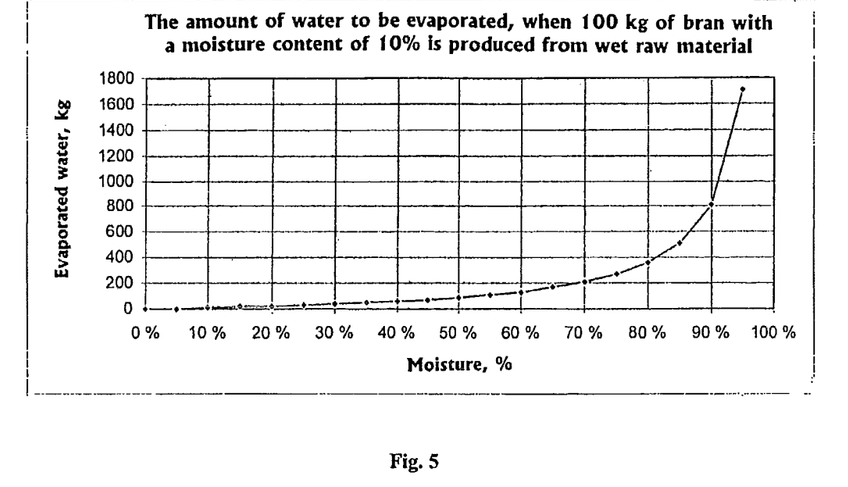
FIG. 5 shows the amounts of water (kg) to be evaporated, when 100 kg of bran with 10% by weight of moisture is produced from wet raw materials, the moisture contents of which vary.

FIG. 5 shows, how many kilos of water must be evaporated, when 100 kg of bran with a moisture content of 10% are produced from wet raw material. Since it is extremely difficult to mechanically remove water from bran fibre containing beta-glucan, a large amount of energy must be used to dry the bran. According to the invention, the bran in the extruder preferably has a water content of 45-55%. In that case, the amount of water that is removed from the bran is minor, and the amount of drying energy needed is small.

By means of the method according to the invention, an essentially inextensible structure in an aqueous environment is provided for the cereal bran product containing beta-glucan. The viscosity of the product is preferably below 200 mPas and its beta-glucan content about 0.75% by weight. The change in viscosity within a shear rate range of 10-800 l/s is preferably below 150 mPas and the β-glucan content 0.75% by weight.

It is particularly preferable to use the product according to the present invention in foodstuffs containing water or in foodstuffs, the manufacture of which requires the use of water.

According to the present invention, the amount of bran product that is obtained in a foodstuff is about 3-150 g per kilo.

The bran product according to the invention can also be used in cosmetic and pharmaceutical products.

EXAMPLES

Example 1

Double Extrusion

Pre-treated oat fibres (Suomen Viljava Oy OBC NEF 18), wherein the beta-glucan had been brought out by dry grinding and the moisture was 9% by weight, was extruded by the Clextral BJ72 device (120 cm). The moisture of the bran in the extruder was 54% by weight and the temperature 60-70° C. The speed of the screw was 120 rmp. The Econase® Ce enzyme was dosed along with the added water to the front end of the extruder at a rate of 1.1 litre/tonne in an hour.

At the dwell stage after the extrusion, the enzyme hydrolyzed the beta-glucan of the oat bran.

The dwell time was 10 minutes and the temperature 40° C. The moisture of the bran was 54% by weight. The hydrolysis was controlled, because the plastic mass decelerates the movement of the enzyme to the vicinity of its substrate. The hydrolysis can be controlled by changing the moisture or the dwell time of the plastic mass.

After the dwell stage, the activity of the enzyme was destroyed at the following extrusion stage by the Clextral BJ72 device (120 cm). The moisture in the extruder was 54% by weight and the temperature 95° C. Thereafter, the product was dried to a moisture content of 12% by weight and ground into a suitable particle size.

The product was assessed by a quick viscosity test, wherein the aqueous solution of 7% by weight of the product was boiled in a water glass in a microwave oven and the heating was stopped, when foam started to form (about 50 sec., 600 W). The sample was stirred and re-boiled, so that foam started to form again (about 10 sec., 600 W). The mixture was cooled and the extensibility was visually assessed. An excess amount of alpha-amylase that did not contain beta-glucanase was added to the extensibility test. Consequently, the extensibility was provided by beta-glucan only. The extensibility of the product caused by beta-glucan was low.

Figure 3:
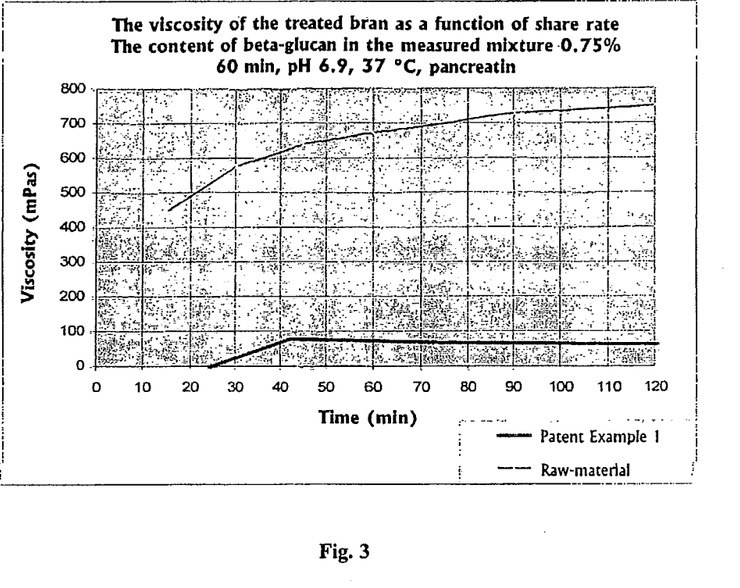
FIG. 3 shows the development of viscosity at a shear rate of 42 l/s.
Figure 4:
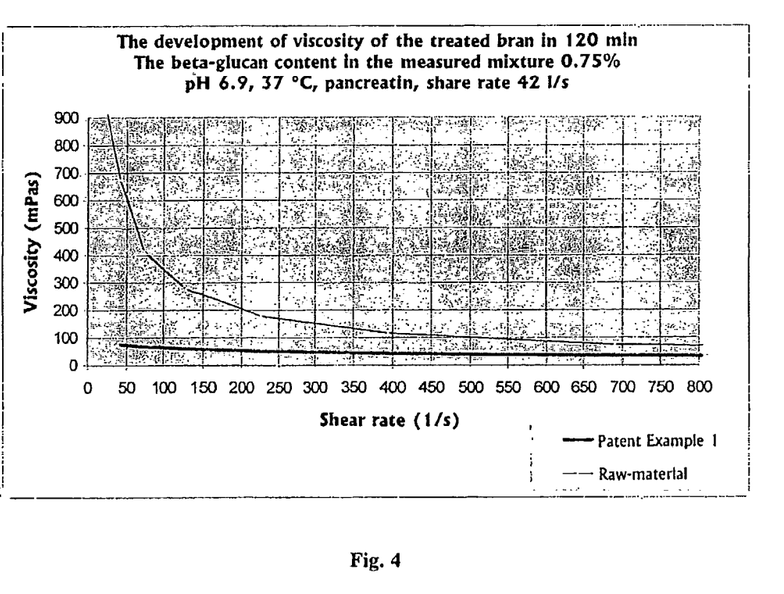
FIG. 4 shows the change in viscosity, when the shear rate changes 10-800 l/s.

The viscosity of the obtained product was measured in the manner described in Example 2 and the results are shown in FIGS. 3 and 4; FIG. 3 shows the development of viscosity as a function of time, and FIG. 4 shows the viscosity as a function of the share rate.

Example 2

Change in Viscosity

The product obtained in Example 1 and the oat fibres that were pre-treated as a reference (the product disclosed in the patent application WO2004/099257) were mixed with water, so that in the mixtures containing oat fibre, the content of beta-glucan in the aqueous solutions was 0.75% by weight.

This mixture, the pH of which was adjusted to pH 6.9, was incubated for 2 hours at a temperature of 37° C. During this time, the development of viscosity was followed (Tappy, L., Gügolz, E. and Würsch, P., Diabetes Care 19, 831-834 (1996)). The viscosity measurements were carried out by the Bohl VOR 88 rheometer. From the mixture, the development of viscosity as a function of time (15-120 min) and at a share rate of 42 l/sec (FIG. 3) was measured. It was observed that the viscosity of the product according to Example 1 was below about 100 mPas.

As shown in FIG. 4, the change in viscosity of the product according to Example 1 within a share rate range of 10-800 l/sec was below 100 mPas after 1 hour of incubation.

Example 3

Single Extrusion with Alpha-Amylase and Cellulase Enzymes

By adding alpha-amylase together with a cellulase enzyme, the extensibility of the β-glucan can be decreased by a single extrusion, which considerably reduces the processing costs.

Oat bran containing 20% by weight of beta-glucan or barley bran containing 18% by weight of beta-glucan was fed into the pre-treatment at a rate of 300 kg an hour. The pre-treatment was carried out by means of fine grinding or processing, so that at least 95% of the particles were smaller than 150 μm. The thermo-mechanical treatment was carried out by extruding by the device described in the previous examples, the moisture being 45% by weight and the temperature about 65° C. The enzymes used comprised Econase® CE, AB Enzymes GmbH, 2 litres/tonne, and thermophilic amylase, Termamyl® SC, from the Novozymes A/S product, 2 litres/tonne. The enzymes were allowed to act for 65 sec. The enzymes were inactivated by increasing the temperature to 95° C. The nozzle feed was carried out at a speed of 1.4 kg/mm2/h. The cutter was used at its maximum speed.

After this, the product was dried. There was no need for a separate grinding, as the bran came out of the extruder in a sufficiently fine-grained form.

The viscosity of the product was quickly estimated according to Example. 1. In the test, it was observed that the extensibility of the product was low.

Example 4

Single Extrusion with Alpha-Amylase and 1.4-Beta-Glucanase Enzymes

Oat bran with 20% by weight of beta-glucan or barley bran with 18% by weight of beta-glucan was fed into the pre-treatment at a rate of 300 kg an hour. The pre-treatment was carried out by means of fine grinding or processing, so that at least 95% of the particles were smaller than 150 μm. The thermo-mechanical treatment was carried out by extruding by the device described in the previous examples, the moisture being 45% by weight and the temperature about 65° C.

The enzymes used comprised thermophilic amylase, Termamyl® SC, Novozymes A/S, 2 litres/tonne, and laminar glass, Laminex® BG, Genencor International, U.S.A., 2 litres/tonne. The enzymes were allowed to act for 65 sec. The enzymes were inactivated by raising the temperature to 95° C. The nozzle feed was carried out at a rate of 1.4 kg/mm²/h. The cutter was used at its maximum speed.

Thereafter, the product was dried. There was no need for a separate grinding, as the bran came out of the extruder in a sufficiently fine form.

The viscosity of the product was quickly estimated according to Example 1. In the test, it was observed that the extensibility of the product was low. However, the structure of the aqueous suspension was longer and more difficult to spoon up than when using the AB Enzymes GmbH Econase enzyme.

Example 5

Pasta Application

An industrial pasta test was arranged in the manner shown in the diagram below (Table 1). The pasta was made of normal or heat-treated wheat, the variety being Semolina, mixing with it 10 or 20% of the inextensible oat bran manufactured by the method according to the invention.

TABLE 1

|  | Drying at normal temperature | | | | Drying at high temperature | | | |
| --- | --- | --- | --- | --- | --- | --- | --- | --- |
|  | Normal semolina | | Heat-treated semolina | | Normal semolina | | Heat-treated semolina | |
| Inextensible oat bran | 10% | 20% | 10% | 20% | 10% | 20% | 10% | 20% |

When carrying out the industrial test, no problems were observed. Drying at the high temperature reduced the yield, when the amount of inextensible oat bran was 10%. When the cooking time of pasta was 5 minutes, its volume, breaking up, appearance, flexibility, breaking strength, smell and viscosity were independent on the amount of beta-glucan.

Example 6

Meat Ball Application

Meat balls of a pilot measure were made according to the recipes of the table below.

TABLE 2

| Recipe | Reference | Inextensible oat bran |
| --- | --- | --- |
| Meat 1 (45% of fat) | 17.5% | 17.5% |
| Meat 2 (20% of fat) | 6% | 6% |
| Broiler chicken | 17.5% | 17.5% |
| Pork rind emulsion | 5.5% | 5.5% |
| Breadcrumbs/inextensible oat bran | 7.10% | 7.10% |
| Soya | 7.75% | 7.75% |
| Potato flour | 1.9% | 1.9% |
| Spices | 3.88% | 3.88% |
| Water | 32.87% | 32.87% |

The raw materials were ground in a meat grinder and fed into a mixer, where mixing was continued for 12 min. At the end of mixing, the temperature was 0° C. The balls were shaped after about an hour and baked after about 1.5 hours. First, the balls were deep-fried (180° C., 50 sec.) and, after that, moved into an oven (180° C., moisture 70%, 8 min). The yield of the balls made of inextensible oat bran was the same as in the reference. The balls made of the inextensible oat bran were softer and, on a sensory basis, as good as or better than the reference balls. The weight of a finished ball was about 18 g (the yield 84%) and it contained about 8.5 g of inextensible oat bran. When the inextensible oat bran contained 14-18% of beta-glucan, one ball contained about 0.2 g of beta-glucan.

The invention claimed is:

1. A method of manufacturing a cereal bran product containing beta-glucan, comprising the following stages:
 pretreating the cereal bran, whereby the beta-glucan is brought out of the cereal bran;
 thermo-mechanically treating the cereal bran, whereby a plastic mass is formed from the cereal bran, wherein the thermo-mechanical treatment is carried out at two stages, wherein the thermo-mechanical treatment stages comprise an extrusion or an expansion process and wherein the moisture of the cereal bran at the thermo-mechanical treatment stages is 20-65% by weight;
 bringing the mass into contact with an enzyme that breaks up beta-glucan with or without an enzyme that breaks up starch;
 inactivating the enzyme(s); and
 drying the bran and, optionally, grinding the bran.

2. The method according to claim 1, wherein the pre-treatment stage comprises crushing the cereal bran into particles by means of mechanical energy, so that in connection with the crushing, at least major part of the cells of the material that contain non-starch polysaccharides is damaged.

3. The method according to claim 1 or 2, wherein at the pre-treatment stage, the cereal bran is crushed into a particle size that is below 200 µm.

4. The method according to claim 2, wherein the crushing at the pre-treatment stage is carried out by extrusion or fine-grinding, by fine-grinding in the separation process of the bran.

5. The method according to claim 1, wherein the temperature at the thermo-mechanical treatment stages is within 40-70° C.

6. The method according to claim 1, wherein between the thermo-mechanical treatment stages and the inactivation stage of the enzyme, there is a dwell stage, wherein the enzyme hydrolyzes the β-glucan.

7. The method according to claim 6, wherein at the dwell stage, the moisture of the mass is about 20-65% by weight, the temperature is about 40-65° C. and the dwell time is about 10 min-2 hours.

8. The method according to claim 1, wherein at the thermo-mechanical treatment stages, the plastic mass formed from the cereal bran is brought into contact with enzymes containing beta-glucanase or materials containing them.

9. The method according to claim 1, wherein the enzyme is dosed in amounts of about $1 \times 10^6 - 1000 \times 10^6$ beta-glucanase units an hour per tonne of bran that is to be treated.

10. The method according to claim 1, wherein in addition to the enzymes that contain beta-glucanase, enzymes containing alpha-amylase or a material containing them are used at the thermo-mechanical processing stages.

11. The method according to claim 1, wherein the enzyme is inactivated by heat.

12. The method according to claim 1, wherein the temperature at the inactivation stage is 90-130° C., and the moisture is within 20-65% by weight.

13. The method according to claim 1, wherein at the drying stage, the mass is dried to a moisture content that is 14% by weight or less.

14. The method according to claim 1, wherein after the drying stage, the bran is ground into a desired roughness.

15. The method according to claim 1, wherein the cereal bran that is treated by the method is partly or fully formed from the grains of oat, barley or rye or the fractions thereof.

16. The method according to claim 15, wherein the cereal bran contains 15-40% by weight of beta-glucan and 5-35% by weight of starch.

* * * * *